(12) United States Patent
Okamoto et al.

(10) Patent No.: US 10,527,569 B2
(45) Date of Patent: Jan. 7, 2020

(54) GAS-SENSOR DIAGNOSING METHOD

(71) Applicant: NGK INSULATORS, LTD., Nagoya-shi, Aichi (JP)

(72) Inventors: Taku Okamoto, Nagoya (JP); Yuki Nakayama, Nagoya (JP); Kosuke Monna, Aichi (JP); Osamu Nakasone, Inabe (JP)

(73) Assignee: NGK INSULATORS, LTD., Nagoya (JP)

( * ) Notice: Subject to any disclaimer, the term of this patent is extended or adjusted under 35 U.S.C. 154(b) by 431 days.

(21) Appl. No.: 15/367,334

(22) Filed: Dec. 2, 2016

(65) Prior Publication Data

US 2017/0167994 A1 Jun. 15, 2017

(30) Foreign Application Priority Data

Dec. 15, 2015 (JP) ................... 2015-244115

(51) Int. Cl.
*G01N 27/02* (2006.01)
*G01N 27/407* (2006.01)

(52) U.S. Cl.
CPC ......... *G01N 27/026* (2013.01); *G01N 27/028* (2013.01); *G01N 27/4071* (2013.01); *G01N 27/4073* (2013.01); *G01N 27/4075* (2013.01)

(58) Field of Classification Search
CPC ............. F02D 41/1495; F02D 41/1454; F01N 2550/00–24; G01N 27/026;

(Continued)

(56) References Cited

U.S. PATENT DOCUMENTS

| 5,433,830 A | 7/1995 | Kawai et al. |
| 6,286,493 B1* | 9/2001 | Aoki ................... F02D 41/1456 123/690 |

(Continued)

FOREIGN PATENT DOCUMENTS

| JP | 6-265522 A | 9/1994 |
| JP | 11-326266 A | 11/1999 |

(Continued)

*Primary Examiner* — Gurpreet Kaur
(74) *Attorney, Agent, or Firm* — Global IP Counselors, LLP

(57) ABSTRACT

Provided is a method of suitably judging necessity of a recovering process carried out on a mixed-potential gas sensor based on an extent of reversible deterioration occurring in a sensing electrode. The method includes the steps of: (a) performing impedance measurement between a sensing electrode exposed to a measurement gas and a reference electrode exposed to a reference atmosphere, which are provided in the gas sensor; and (b) judging necessity of a recovering process based on electrode reaction resistance or a diagnosis parameter correlating with the electrode reaction resistance wherein the electrode reaction resistance and the diagnosis parameter are obtained based on a result of the impedance measurement. The two steps are intermittently or periodically repeated during use of the gas sensor, and it is judged that a recovering process is necessary when the judge parameter satisfies a predetermined threshold condition in the step (b).

2 Claims, 7 Drawing Sheets

(58) Field of Classification Search
CPC ............. G01N 27/028; G01N 27/4071; G01N 27/4073; G01N 27/4075; G01N 27/4175
See application file for complete search history.

(56) References Cited

U.S. PATENT DOCUMENTS

| | | | |
|---|---|---|---|
| 7,285,204 B2 | 10/2007 | Iida et al. | |
| 8,721,854 B2 | 5/2014 | Aoki et al. | |
| 2011/0016949 A1* | 1/2011 | Sasaki | G01N 27/4175 73/23.31 |

FOREIGN PATENT DOCUMENTS

| | | |
|---|---|---|
| JP | 3855877 B2 | 9/2006 |
| JP | 3855979 B2 | 9/2006 |
| JP | 4580115 B2 | 9/2010 |
| JP | 4669369 B2 | 1/2011 |
| JP | 2014-48279 A | 3/2014 |

* cited by examiner

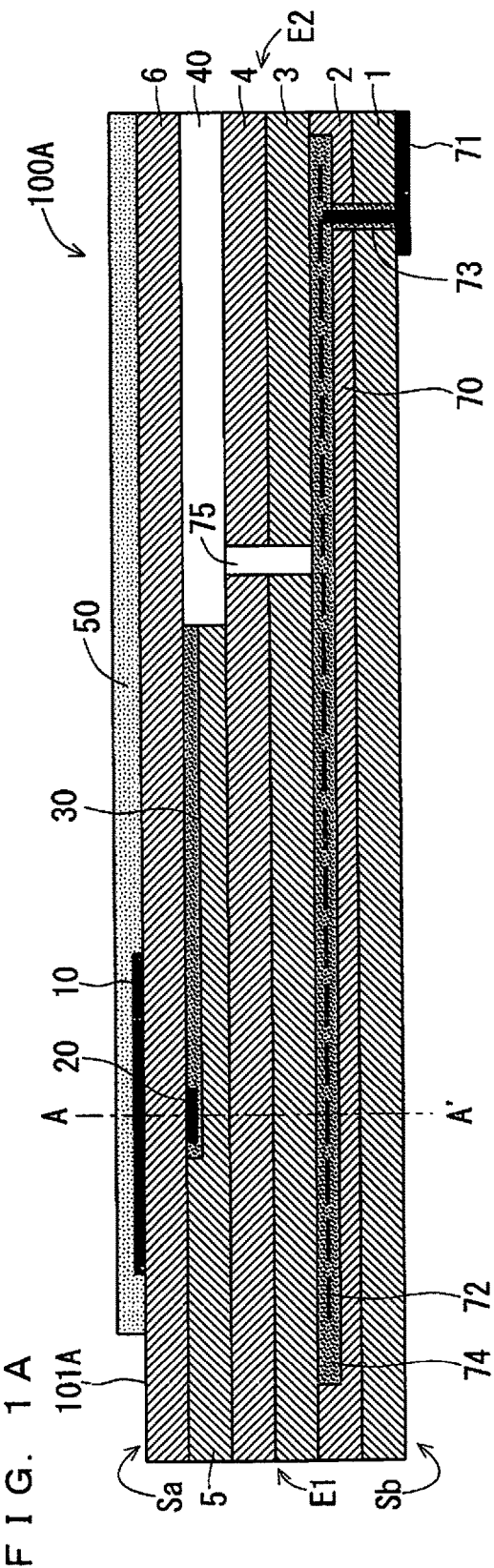

GAS-SENSOR DIAGNOSING METHOD

BACKGROUND OF THE INVENTION

Field of the Invention

The present invention relates to a process of diagnosing a state of a mixed-potential gas sensor, and more particularly to a process of diagnosing a deterioration state of a sensing electrode of a gas sensor.

Description of the Background Art

Gas sensors that sense a predetermined gas component in a measurement gas such as an exhaust gas, for example, to determine its concentration come in various types such as a semiconductor gas sensor, a catalytic combustion gas sensor, an oxygen-concentration difference sensing gas sensor, a limiting current gas sensor, and a mixed-potential gas sensor. Some of these gas sensors are obtained by providing electrodes containing a noble metal or a metal oxide as its main constituent to a sensor element mainly made of ceramic is a solid electrolyte such as zirconia.

As is also well-known, in a gas sensor which includes a sensor element mainly made of ceramic such as zirconia, a gas component in a measurement gas or a poisoning substance is adhered to the surface of the electrode due to long-term use, or a composing substance of the electrode is sintered due to exposure of the electrode to a high-temperature atmosphere, so that an output value may vary although a concentration of a gas component to be measured in a measurement gas is constant.

Among the above-stated causes for output change of a gas sensor, adhesion of a poisoning substance and sintering of a constituting material of the electrode are irreversible phenomena, and it is considered to be difficult to cope directly with change in output value due to electrode deterioration (irreversible deterioration) caused by those phenomena.

On the other hand, it is possible to cope with output change due to adhesion (adsorption) of a gas component in a measurement gas to the surface of the electrode, by carrying out a predetermined recovering process and removing the adsorbed gas component. That is, such output change is caused due to electrode deterioration (reversible deterioration) caused by a reversible factor. With regard to a gas sensor subjected to such reversible deterioration, execution of a recovering process would allow an original (initial) output value to be re-attained, or would allow an output value as close to the original output value as possible to be obtained.

Examples of the foregoing recovering process include an electrical process (for example, refer to Japanese Patent Application Laid-Open No. 6-265522 (1994) and Japanese Patent No. 3855979), and a heating process (for example, refer to Japanese Patent Application Laid-Open No. 11-326266 (1999)).

The electrical process is a method for recovering output by alternately applying positive and negative potentials between electrodes that are paired through a solid electrolyte, so as to refine the electrode or to desorb an absorbed substance.

On the other hand, the heating process is a method for recovering output with exposure of an adsorbed substance or a poisoning substance to a high temperature to desorb or burn (oxidize) the substance.

Also, a method of diagnosing presence or absence of an anomaly deterioration for various gas sensors is already known (for example, refer to Japanese Patent No. 4580115, Japanese Patent No. 3855877, Japanese Patent No. 4669369, and Japanese Patent Application Laid-Open No. 2014-48279).

Japanese Patent No. 4580115 discloses a technique for judging presence or absence of an anomaly from a detected value of internal resistance of a solid electrolytic material forming a gas sensor based on an impedance model, in order to prevent a heater from being excessively heated due to an anomaly (increase in resistance) of the solid electrolytic material.

Japanese Patent No. 3855877 discloses a deterioration detection apparatus which includes air-fuel ratio detection means including a solid electrolytic element, means for detecting deterioration of the air-fuel ratio detection means by comparing output values which are respectively provided in cases where different temperatures are set for the solid electrolytic element, temperature control means for controlling a temperature of the solid electrolytic element, and means for detecting a failure in the temperature control means.

Japanese Patent No. 4669369 discloses an apparatus which periodically measures internal impedance of a sensor element, to judge that a failure such as a short circuit or disconnection occurs in the sensor element when a difference value resulted from the periodical measurement exceeds a threshold.

Japanese Patent Application Laid-Open No. 2014-48279 discloses a gas-sensor control apparatus which makes an atmosphere within a measurement chamber included in a detection element of a gas sensor into two different states, measures element resistance in the respective states, and detects presence or absence of deterioration or an extent of deterioration in the detection element based on a magnitude of a difference value between the measured values.

What is a difficult thing in continually using a gas sensor in which the above-stated output change occurs is to judge what timing is proper for carrying out a recovering process. This is because, if a recovering process is carried out more frequently than necessary, sintering of a material forming an electrode becomes conspicuous unfavorably, while reduction in a sensor output which is caused due to adsorption of a gas component in a measurement gas into a surface of the electrode is prevented. This results in an issue of how reversible deterioration of an electrode can be appropriately grasped. The reason is that, as long as a recovering process is carried out promptly in a case where it is judged that an electrode is reversibly deteriorated to an extent that the recovering process is necessary, a deteriorated state is canceled, so that a sensor output which is reduced is recovered.

While each of Japanese Patent Application Laid-Open No. 6-265522 (1994), Japanese Patent No. 3855979, and Japanese Patent Application Laid-Open No. 11-326266 (1999) discloses a recovering process, none of the above-cited patent literatures discloses or suggests how a deterioration state of an electrode is judged with regard to a gas sensor which is continually used.

Also, in a diagnosing method disclosed in each of Japanese Patent No. 4580115, Japanese Patent No. 3855877, and Japanese Patent No. 4669369, and Japanese Patent Application Laid-Open No. 2014-48279, there is neither disclosure nor suggestion about determinatioFIGSn of a timing to carry out a recovering process, based on an extent of reversible deterioration of an electrode.

SUMMARY OF THE INVENTION

The present invention relates to a method of diagnosing a state of a mixed-potential gas sensor, and more particularly to a method of diagnosing a deterioration state of a sensing electrode of a gas sensor.

According to the present invention, a gas-sensor diagnosing method of judging necessity of a recovering process carried out on a mixed-potential gas sensor for recovering an output of the gas sensor includes the steps of: (a) performing impedance measurement between a sensing electrode exposed to an atmosphere of a measurement gas and a reference electrode exposed to a reference atmosphere, which are provided in the gas sensor; and (b) judging necessity of the recovering process based on electrode reaction resistance in the gas sensor or a diagnosis parameter which is a parameter correlated with the electrode reaction resistance, the electrode reaction resistance and the diagnosis parameter being obtained based on a result of the impedance measurement. The step (a) and the step (b) are intermittently or periodically repeated during use of the gas sensor, and it is judged that the recovering process is necessary when the diagnosis parameter satisfies a predetermined threshold condition in the step (b).

Preferably, in the step (a), the impedance measurement is performed by application of an alternating voltage between the sensing electrode and the reference electrode with a frequency being varied within a frequency range in which a Nyquist diagram for the electrode reaction resistance is allowed to be produced, and in the step (b), the electrode reaction resistance is calculated based on the Nyquist diagram produced based on a result of the impedance measurement, and it is judged that the recovering process is necessary when the calculated electrode reaction resistance is equal to, or smaller than, a predetermined threshold.

Alternatively, preferably, the gas-sensor diagnosing method according to the present invention further includes the step of (c), prior to the step (a), specifying a diagnosis frequency which is a frequency of an alternating voltage used in the impedance measurement in the step (a), by performance of a preliminary impedance measurement in which an alternating voltage is applied between the sensing electrode and the reference electrode with a frequency being varied within a predetermined frequency range in which a Bode diagram for a phase angle is allowed to be produced. In the step (a), the impedance measurement is performed by application of an alternating voltage at the diagnosis frequency, and in the step (b), it is judged that the recovering process is necessary when a value of a phase angle which is obtained by the impedance measurement is a value closer to 0° than a predetermined threshold.

Alternatively, preferably, the gas-sensor diagnosing method according to the present invention further includes the step of (c), prior to the step (a), specifying a diagnosis frequency which is a frequency of an alternating voltage used in the impedance measurement in the step (a), by performance of a preliminary impedance measurement in which an alternating voltage is applied between the sensing electrode and the reference electrode with a frequency being varied within a predetermined frequency range in which a Bode diagram for an absolute value of impedance is allowed to be produced. In the step (a), the impedance measurement is performed by application of an alternating voltage at the diagnosis frequency, and in the step (b), it is judged that the recovering process is necessary when a value of a common logarithm of an absolute value of impedance, which is obtained by the impedance measurement, is equal to, or smaller than, a predetermined threshold.

According to the present invention, it is possible to judge necessity of a recovering process for recovering an output which varies due to reversible deterioration occurring in a sensing electrode of a mixed-potential gas sensor based on an extent of the reversible deterioration occurring in the sensing electrode, so that a recovering process can be carried out at a suitable point in time.

Thus, an object of the present invention is to provide a method of diagnosing a mixed-potential gas sensor, which allows necessity of a recovering process for the mixed-potential gas sensor to be suitably judged based on an extent of reversible deterioration occurring in a sensing electrode.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 1A and 1B are cross-sectional diagrams schematically showing a configuration of a gas sensor;

DESCRIPTION OF THE PREFERRED EMBODIMENTS

Figure 2A:
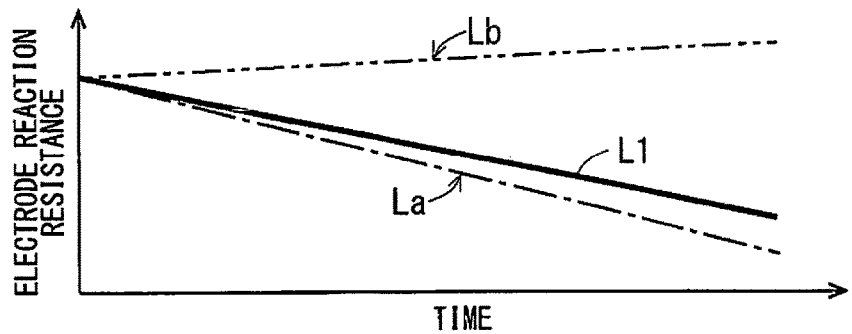
FIGS. 2A and 2B are views schematically showing variation of reaction resistance with time in a mixed-potential gas sensor.

Example of Configuration of a Gas Sensor

FIGS. 1A and 1B are cross-sectional diagrams schematically showing a configuration of a gas sensor 100A as an example of a diagnosis target in a diagnosing method according to the present preferred embodiment. The diagnosing method according to the present preferred embodiment is, roughly speaking, a method of judging necessity of a recovering process for recovering a sensor output which is reduced due to continual use of the gas sensor 100A.

FIG. 1A is a vertical sectional view of a sensor element 101A, which is a main component of the gas sensor 100A, taken along the longitudinal direction of the sensor element 101A. FIG. 1B is a view including a cross-section of the sensor element 101A perpendicular to the longitudinal direction of the sensor element 101A at a position A-A' of FIG. 1A.

The gas sensor 100A according to the first configuration of the present invention is a so-called mixed-potential gas sensor. Generally speaking, the gas sensor 100A determines the concentration of a gas component, which is a measurement target, of a measurement gas using a potential difference that occurs between a sensing electrode 10, which is provided on the surface of the sensor element 101A mainly made of ceramic that is an oxygen-ion conductive solid electrolyte such as zirconia (ZrO2), and a reference electrode 20, which is provided inside the sensor element 101A, due to a difference in the concentration of the gas component between the portions near the electrodes based on the principle of mixed potential.

More specifically, the gas sensor 100A preferably determines the concentration of a predetermined gas component of a measurement gas, where the measurement gas is an exhaust gas present in an exhaust pipe of an internal combustion engine such as a diesel engine or a gasoline engine. In this specification, description will be given of an example case where a predetermined gas component being a measurement target is an unburned hydrocarbon gas. In such a case, examples of the unburned hydrocarbon gas include carbon monoxide (CO) in addition to typical hydrocarbon gases (gases classified as hydrocarbons in terms of chemical formula) such as C2H4, C3H6, and n-C8. In the presence of a plurality of unburned hydrocarbon gases in a measurement gas, a potential difference occurring between the sensing electrode 10 and the reference electrode 20 is a value reflecting all the plurality of unburned hydrocarbon gases, and thus, a concentration value to be determined is also a total sum of the concentrations of the plurality of unburned hydrocarbon gases.

The sensor element 101A mainly includes a reference gas introduction layer 30, a reference gas introduction space 40, and a surface protective layer 50 in addition to the sensing electrode 10 and the reference electrode 20 described above.

In the present preferred embodiment, the sensor element 101A has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 1A and 1B. The sensor element 101A additionally includes other components mainly between these layers or on an outer peripheral surface of the element. The solid electrolytes constituting these six layers are fully airtight. Such a sensor element 101A is manufactured by, for example, laminating ceramic green sheets corresponding to the individual layers, which have been subjected to a predetermined process and printing of a circuit pattern, and further, by integrating the laminated layers through firing.

The gas sensor 100A does not necessarily need to include the sensor element 101A formed of such a laminated body including the six layers. The sensor element 101A may be formed as a laminated body having more or fewer layers or may not have a laminated structure.

In the following description, for convenience' sake, the surface located as the upper surface of the sixth solid electrolyte layer 6 in FIGS. 1A and 1B is referred to as a front surface Sa of the sensor element 101A, and the surface located as the lower surface of the first solid electrolyte layer 1 in FIGS. 1A and 1B is referred to as a rear surface Sb of the sensor element 101A. In the determination of the concentration of the unburned hydrocarbon gas in a measurement gas with the gas sensor 100A, a predetermined range starting from a distal end E1 being one end of the sensor element 101A, which includes at least the sensing electrode 10, is disposed in a measurement gas atmosphere; the other portion including a base end E2 opposite to the distal end E1 is disposed so as not to be in contact with the measurement gas atmosphere.

The sensing electrode 10 is an electrode for sensing a measurement gas. The sensing electrode 10 is formed as a porous cermet electrode made of Pt containing a predetermined ratio of Au, namely, Pt—Au alloy and zirconia. The sensing electrode 10 is provided in a substantially rectangular shape in plan view at a position closer to the distal end E1 that is one end in the longitudinal direction of the sensor element 101A on the front surface Sa of the sensor element 101A. The gas sensor 100A is placed such that, in its use, the sensor element 101A corresponding to at least the portion in which the sensing electrode 10 is provided is exposed to a measurement gas.

The catalytic activity of the sensing electrode 10 against combustion of an unburned hydrocarbon gas is disabled in a predetermined concentration range by preferably determining the composition of the Pt—Au alloy being its constituent material. That is, the combustion reaction of an unburned hydrocarbon gas is prevented or reduced in the sensing electrode 10. In the gas sensor 100A, accordingly, the potential of the sensing electrode 10 selectively varies with respect to (has correlation with) the unburned hydrocarbon gas in the concentration range, in accordance with its concentration. In other words, the sensing electrode 10 is provided so as to have high dependence of potential on concentration for an unburned hydrocarbon gas while having low dependence of potential on concentration for other components of the measurement gas.

More specifically, in the sensor element 101A of the gas sensor 100A according to the present preferred embodiment, the sensing electrode 10 is provided so as to have a preferably determined Au abundance ratio in the surface of the Pt—Au alloy particle included in the sensing electrode 10, thereby exhibiting a strong dependence of potential on concentration in at least part of a concentration range of 0 ppmC to 1000 ppmC, for example. This means that the sensing electrode 10 is provided to preferably determine the concentration of an unburned hydrocarbon gas in the foregoing concentration range. For example, when the Au abundance ratio is set at 0.7 or more, an unburned hydrocarbon gas with a concentration in a range of 4000 ppmC or lower can be suitably sensed. When the Au abundance ratio is set at 0.1 or more and less than 0.7, an unburned hydrocarbon gas with a concentration in a range of 4000 ppmC or higher can be suitably sensed.

In this specification, the Au abundance ratio means an area ratio of a portion covered with Au to a portion at which Pt is exposed in the surface of noble metal (Pt—Au alloy) particles forming the sensing electrode 10. In this specification, an Au abundance ratio is calculated from peak intensities of detection peaks for Au and Pt which are obtained by X-ray photoelectron spectroscopy (XPS), with the use of a relative sensitivity coefficient method. When the area of the portion where Pt is exposed is equal to the area of the portion covered with Au, the Au abundance ratio is 1.

The reference electrode 20 is an electrode having a substantially rectangular shape in plan view, which is provided inside the sensor element 101A and serves as a reference in the determination of the concentration of the measurement gas. The reference electrode 20 is provided as a porous cermet electrode of Pt and zirconia.

It suffices that the reference electrode 20 has a porosity of 10% or more and 30% or less and a thickness of 5 μm or more and 15 μm or less. The plane size of the reference electrode 20 may be smaller than that of the sensing electrode 10 as illustrated in FIGS. 1A and 1B, or may be equal to that of the sensing electrode 10 as in a second configuration, which will be described below (see FIGS. 3A and 3B).

The reference gas introduction layer 30 is a layer made of porous alumina, which is provided inside the sensor element 101A to cover the reference electrode 20. The reference gas introduction space 40 is an internal space provided near the base end E2 of the sensor element 101A. Air (oxygen), serving as a reference gas in the determination of the concentration of an unburned hydrocarbon gas, is externally introduced into the reference gas introduction space 40.

The reference gas introduction space 40 and the reference gas introduction layer 30 are in communication with each other, and accordingly, in the use of the gas sensor 100A, the surrounding of the reference electrode 20 is always filled with air (oxygen) through the reference gas introduction space 40 and the reference gas introduction layer 30. During the use of the gas sensor 100A, thus, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even when the sensing electrode 10 is exposed to the measurement gas.

In the case illustrated in FIGS. 1A and 1B, the reference gas introduction space 40 is provided in such a manner that part of the fifth solid electrolyte layer 5 is in communication with the exterior on the base end E2 of the sensor element 101A. The reference gas introduction layer 30 is provided so as to extend in the longitudinal direction of the sensor element 101A between the fifth solid electrolyte layer 5 and the sixth solid electrolyte layer 6. The reference electrode 20 is provided under the center of gravity of the sensing electrode 10 with reference to FIGS. 1A and 1B.

The surface protective layer 50 is a porous layer made of alumina, which is provided so as to cover at least the sensing electrode 10 on the front surface Sa of the sensor element 101A. The surface protective layer 50 is provided as an electrode protective layer that prevents or reduces the degradation of the sensing electrode 10 due to continuous exposure to a measurement gas during the use of the gas sensor 100A. In the case illustrated in FIG. 1A, the surface protective layer 50 is provided so as to cover not only the sensing electrode 10 but also substantially the entire front surface Sa of the sensor element 101A except for a predetermined range starting from the distal end E1.

As illustrated in FIG. 1B, the gas sensor 100A is equipped with a potentiometer 60 capable of measuring a potential difference between the sensing electrode 10 and the reference electrode 20. Although FIG. 1B schematically illustrates wiring of the sensing electrode 10, the reference electrode 20, and the potentiometer 60, in an actual sensor element 101A, connection terminals (not shown) are provided correspondingly to the respective electrodes on the front surface Sa or the rear surface Sb on the base end E2 side, and wiring patterns (not shown), which connect the respective electrodes and their corresponding connection terminals, are formed on the front surface Sa and inside the element. The sensing electrode 10 and the reference electrode 20 are electrically connected with the potentiometer 60 through the wiring patterns and the connection terminals. Hereinbelow, a potential difference between the sensing electrode 10 and the reference electrode 20, which is measured by the potentiometer 60, is also referred to as a sensor output.

The sensor element 101A further includes a heater part 70, which performs temperature control of heating the sensor element 101A and maintaining the temperature of the sensor element 101A, to enhance the oxygen ion conductivity of the solid electrolyte. The heater part 70 includes a heater electrode 71, a heater 72, a through hole 73, a heater insulating layer 74, and a pressure diffusion hole 75.

The heater electrode 71 is an electrode formed while being in contact with the rear surface Sb of the sensor element 101A (in FIGS. 1A and 1B, the lower surface of the first solid electrolyte layer 1). The heater part 70 can be powered externally by the heater electrode 71 connected with an external power supply (not shown).

The heater 72 is an electric resistor provided inside the sensor element 101A. The heater 72 is connected with the heater electrode 71 through the through hole 73 and generates heat by being powered externally via the heater electrode 71 to heat the solid electrolytes forming the sensor element 101A and maintain their temperatures.

In the case illustrated in FIGS. 1A and 1B, the heater 72 is buried while being vertically sandwiched between the second solid electrolyte layer 2 and the third solid electrolyte layer 3 so as to extend from the base end E2 to the position below the sensing electrode 10 near the distal end E1. This enables the adjustment of the entire sensor element 101A to the temperature at which the solid electrolytes are activated.

The heater insulating layer 74 is an insulating layer formed of an insulator such as alumina on the upper and lower surfaces of the heater 72. The heater insulating layer 74 is formed for electrical insulation between the second solid electrolyte layer 2 and the heater 72 and for electrical insulation between the third solid electrolyte layer 3 and the heater 72.

The pressure diffusion hole 75 is a part provided to penetrate the third solid electrolyte layer 3 and the fourth solid electrolyte layer 4 and to be in communication with the reference gas introduction space 40, and is formed to mitigate an internal pressure rise associated with a temperature rise in the heater insulating layer 74.

In the determination of the concentration of an unburned hydrocarbon gas in a measurement gas using the gas sensor 100A having such a configuration, as described above, air (oxygen) is supplied to the reference gas introduction space 40, with the sensor element 101A in only a predetermined range, which starts from the distal end E1 and includes at least the sensing electrode 10, being disposed in a space containing a measurement gas, and with the sensor element 101A on the base end E2 being apart from the space. The heater 72 heats the sensor element 101A to an appropriate temperature from 400° C. to 800° C., preferably from 500° C. to 700° C., more preferably from 500° C. to 600° C.

In such a state, a potential difference occurs between the sensing electrode 10 exposed to the measurement gas and the reference electrode 20 exposed to the air. As described above, however, the potential of the reference electrode 20 disposed in the air (having a constant oxygen concentration) atmosphere is maintained at a constant potential, whereas the potential of the sensing electrode 10 selectively has a dependence on concentration for the unburned hydrocarbon gas of the measurement gas. The potential difference (sensor output) is thus substantially a value according to the composition of the measurement gas present around the sensing electrode 10. Therefore, a certain functional relationship (referred to as sensitivity characteristics) holds between the concentration of the unburned hydrocarbon gas and the sensor output. In the description below, such sensitivity characteristics may also be referred to as, for example, sensitivity characteristics for the sensing electrode 10.

In the actual determination of the concentration of an unburned hydrocarbon gas, in advance, a plurality of different mixed gases, each of which has a known concentration of an unburned hydrocarbon gas, are used as the measurement gas, and the sensitivity characteristics are experimentally identified by performing a measurement on the sensor output for each measurement gas. In the actual use of the gas sensor 100A, accordingly, an operation processor (not shown) converts the sensor output, which varies from moment to moment in accordance with the concentration of an unburned hydrocarbon gas in a measurement gas, into the concentration of the unburned hydrocarbon gas based on the sensitivity characteristics. The concentration of the unburned hydrocarbon gas in the measurement gas can thus be determined almost in real time.

<Aging Variation of Electrode Reaction Resistance, and Recovering Process>

Figure 2B:
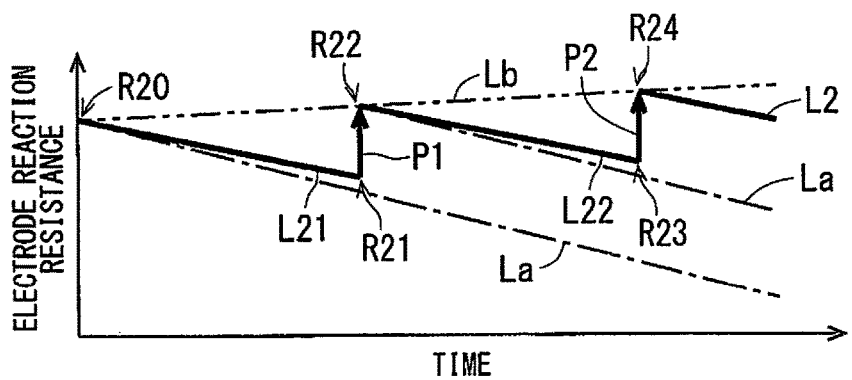

FIGS. 2A and 2B are views schematically showing variation of reaction resistance (electrode reaction resistance) with time in a mixed-potential gas sensor like the gas sensor 100A.

Conventionally, during continual use of a mixed-potential gas sensor, reaction resistance has a tendency to be reduced with time as indicated by a straight line L1 in FIG. 2A. Such reduction in reaction resistance causes a sensor output to be reduced with time.

Figure 3:
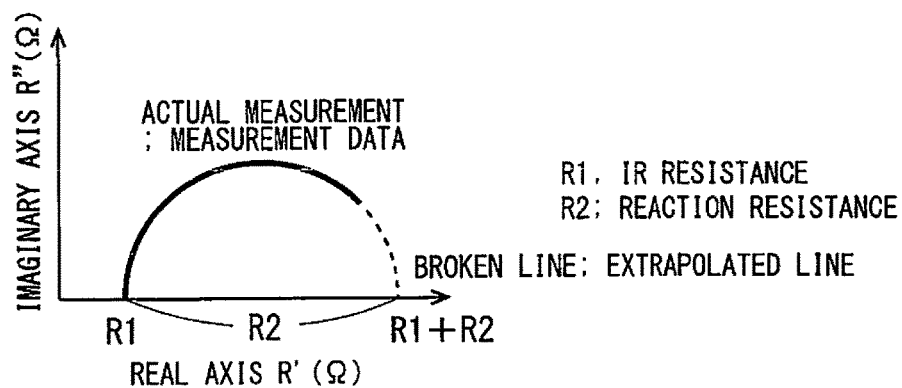
FIG. 3 is a schematic representation of a Nyquist diagram for explaining reaction resistance.

Reaction resistance is obtained from a Nyquist diagram on which a result of two-terminal impedance measurement performed by application of an alternating voltage between a sensing electrode and a reference electrode in a gas sensor with a frequency being varied is plotted, with a horizontal axis being defined as a real axis (R' axis, unit: $\Omega$) and a vertical axis being defined as an imaginary axis (R" axis, unit: $\Omega$). FIG. 3 is a schematic representation of a Nyquist diagram for explaining derivation of reaction resistance.

More specifically, as a result of plotting of actual-measurement data, a curve in a shape of an arc having an origin on one side at a point on a real axis (R', R")=(R1, 0) is provided as shown in FIG. 3. Then, when R' coordinate value of an end point on the other side of the curve, or R' coordinate value of an extrapolation point extrapolated from the end point on the real axis R', is expressed as R1+R2, an increment R2 with respect to the R' coordinate value R1 is reaction resistance. Additionally, the value R1 is IR resistance (insulation resistance), which corresponds to material resistance of a solid electrolyte forming a sensor element, for example, in a case of a mixed-potential gas sensor like the gas sensor 100A. Accordingly, if an anomaly occurs in a solid electrolyte, not a value R2 but a value R1 varies.

The inventors of the present invention have found that whereas adhesion (adsorption) of a gas component in a measurement gas to a surface of a sensing electrode has a tendency to reduce reaction resistance with time as indicated by a straight line La in FIG. 2A, an irreversible phenomenon (irreversible deterioration) such as adhesion of a poisoning substance or sintering of a material forming a sensing electrode has a tendency to increase reaction resistance with time as indicated by a straight line Lb in FIG. 2A, while diligently investigating and studying the above-described reduction in reaction resistance and sensor output with time. Further, the inventors have acquired knowledge that the reason why actual reaction resistance is reduced with time as indicated by the straight line L1 and a sensor output is accordingly reduced with time is that reduction in reaction resistance due to adsorption of a gas component indicated by the straight line La is steeper than, and therefore dominant over, increase in reaction resistance due to an irreversible phenomenon indicated by the straight line Lb. Additionally, while variation of reaction resistance with time is indicated by straight lines in FIGS. 2A and 2B in order to represent tendencies of increase and reduction in a simplified manner, actual variation with time does not necessarily occur linearly.

Conventionally-performed known recovering processes such as an electrical process disclosed in Japanese Patent Application Laid-Open No. 6-265522 (1994) and Japanese Patent No. 3855979 and a heating process disclosed in Japanese Patent Application Laid-Open No. 11-326266 (1999), for example, are intended for cancellation of reduction in sensor output which is caused due to adsorption of a gas component into a surface of a sensing electrode, out of the above-described reductions.

In FIG. 2B, a solid line L2 indicates variation of reaction resistance with time in a case where a recovering process is carried out at some midpoint during use of a gas sensor. In the case shown in FIG. 2B, like the case shown in FIG. 2A, reaction resistance having an initial value R20 is reduced with time along a line segment L21 which is defined by a balance between the straight line La indicating reduction in reaction resistance caused due to adsorption (reversible deterioration) of a gas component into a surface of a sensing electrode and the straight line Lb indicating increase in reaction resistance caused due to irreversible deterioration in a gas sensor. For example, if a recovering process P1 is carried out at a point in time when reaction resistance has a certain value R21 as shown in FIG. 2B, decrement caused due to adsorption of a gas component is canceled, and a sensor output is recovered. However, also irreversible deterioration proceeds with time in a sensing electrode, so that reaction resistance has a value R22 on the straight line Lb, not the initial value R20, after a recovering process. This means that a recovering process achieves the same state as a state in which only irreversible deterioration occurs with time.

After that, as a gas sensor continues to be used, a value of reaction resistance is reduced with time along a line segment L22 defined by a balance between the straight line La and the straight line Lb again. However, if a recovering process P2 is carried out again at a point in time when reaction resistance has a value R23, decrement caused due to adsorption of a gas component is canceled again, and reaction resistance is recovered to a value R24 on the straight line Lb.

Thereafter, by repetition of a recovering process in a similar manner at appropriate points in time, reaction resistance, together with a sensor output, which is once reduced, is recovered again after each recovering process. Moreover, a state of a sensing electrode after each recovering process is equivalent to a state where only irreversible deterioration proceeds. In other words, reduction in reaction resistance with time after a recovering process is once carried out starts from a state where only irreversible deterioration proceeds.

However, depending on a way in which a gas sensor is actually used, irreversible deterioration may proceed only at an extremely moderate pace, as compared to reversible deterioration. In those cases, a state of a sensing electrode after a recovering process can be regarded as being almost identical to an initial state.

<Method of Judging Necessity of Recovering Process>

Next, a method of judging necessity of recovering process will be described. Since a recovering process is intended to recover a sensor output which is reduced with time, necessity of a recovering process may be judged based on a behavior of a sensor output. In this regard, as described above, a process carried out as a recovering process itself may cancel reduction in reaction resistance causing reduction in sensor output, with elimination of adsorption of a gas component into a sensing electrode, i.e., elimination of reversible deterioration. However, variation in sensor output is also affected by irreversible deterioration which is not a target of the recovering process and increases reaction resistance with time. Accordingly, in order to achieve elimination of reversible deterioration which is an original effect provided by a recovering process, at a suitable timing, it is preferable to carry out the recovering process based on a value of reaction resistance which is reduced, reflecting a deterioration state of a sensing electrode which is caused due to reversible deterioration.

Moreover, it is not preferable to carry out a recovering process excessively, because sintering of a material forming a sensing electrode would be promoted, so that increase in reaction resistance which is caused due to irreversible deterioration, which is shown as being moderate in FIGS. 2A and 2B, may become much steeper. On the other hand, it is not preferable to carry out a recovering process at excessively long intervals, because reaction resistance, as well as a sensor output, would be significantly reduced, resulting in impaired measurement accuracy.

In view of the foregoing matters, a method of judging necessity of a recovering process according to the present preferred embodiment includes three manners as follows.

(First Manner: Judgement Based on Nyquist Diagram)

As schematically shown in FIG. 3, reaction resistance is specified from a Nyquist diagram obtained based on a result of two-terminal impedance measurement in which an alternating voltage is applied between a sensing electrode and a reference electrode in a gas sensor with a frequency being varied. Accordingly, if a value of reaction resistance obtained from a Nyquist diagram is below a predetermined threshold, it indicates that deposition of a gas component on a sensing electrode proceeds to an extent of affecting measurement accuracy, so that it is judged that a recovering process is necessary.

Figure 4:
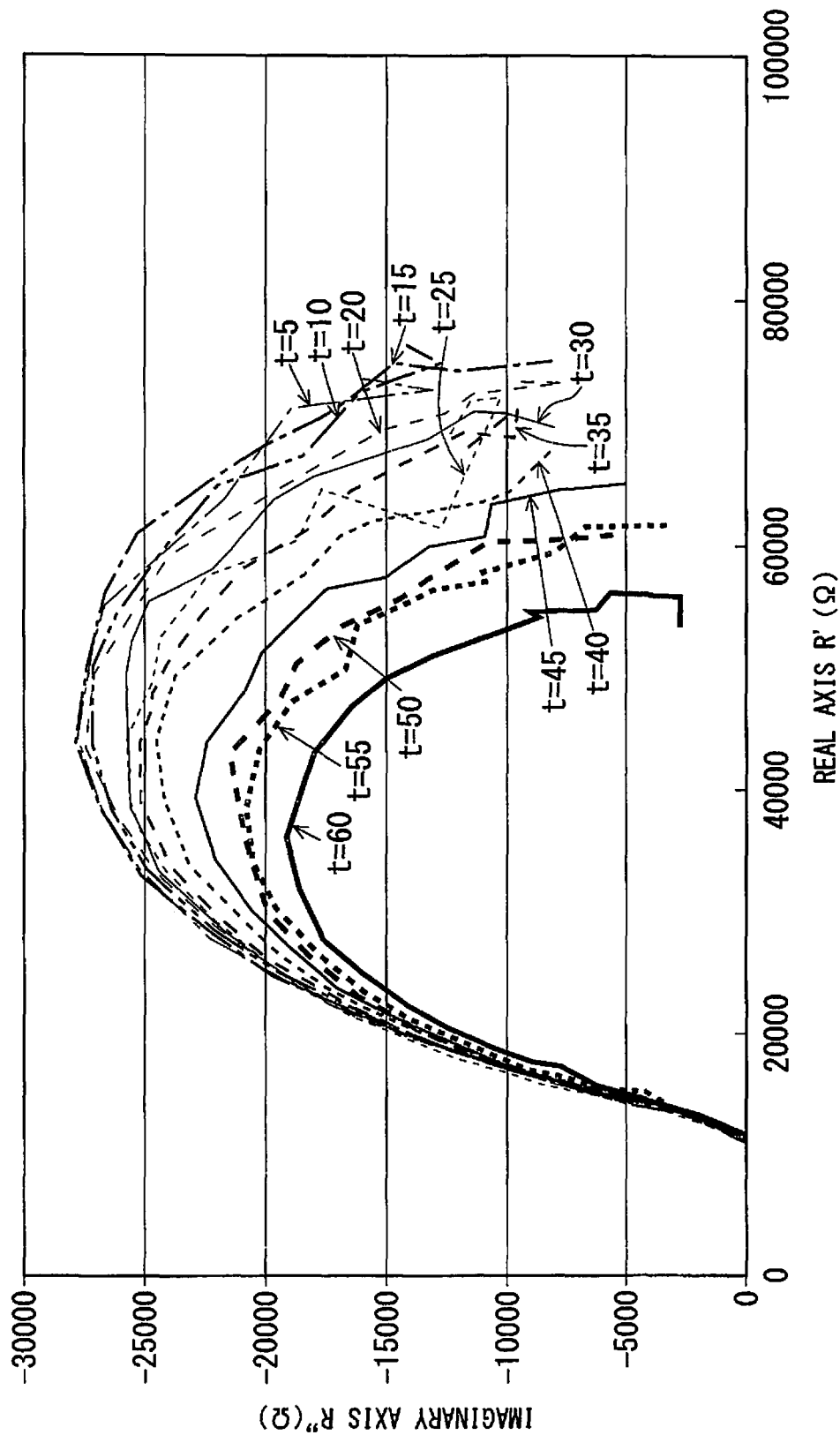
FIG. 4 is a view showing time-series variation of respective Nyquist diagrams obtained from two-terminal impedance measurement between a sensing electrode and a reference electrode which is repeatedly performed with the sensing electrode being kept exposed to a gas atmosphere containing an unburned hydrocarbon gas.

FIG. 4 is a view showing time-series variation of respective Nyquist diagrams obtained when two-terminal impedance measurement between the sensing electrode 10 and the reference electrode 20 which is periodically repeated while the sensing electrode 10 is kept exposed to a gas atmosphere containing an unburned hydrocarbon gas and the gas sensor 100A is driven with a temperature of a sensor element being set at 600° C. Conditions of measurement are as follows.

Gas atmosphere (produced with the use of a model gas apparatus):
$C_2H_4$ (corresponding to an unburned hydrocarbon gas)=1000 ppm (=2000 ppmC);
$O_2$=10%;
$H_2O$=5%;
$N_2$=residual;
Impedance measurement:
Frequency=0.1 Hz to 1 MHz;
Amplitude=10 mV;
Bias voltage for open-circuit voltage (OCV)=0;
Measurement interval . . . at five-minute intervals in sixty minutes from a time of gas introduction (t=5 to 60)

Additionally, a concentration of $C_2H_4$ in a gas atmosphere is set at 2000 ppmC which is higher than a concentration of an unburned hydrocarbon gas in an exhaust gas exhausted from a general internal combustion engine, in order to accelerate adsorption of $C_2H_4$ into the sensing electrode 10. Also, a measurement interval for impedance measurement is set at every five minutes in accordance with such acceleration of adsorption, and a longer measurement interval may be set for actual use of a gas sensor.

From FIG. 4, it can be seen that whereas the respective Nyquist diagrams are similar to one another in the respect that a curve in a shape of an arc starting from a position of approximately 1150 (Ω) on a real axis is formed, a coordinate value on a real axis of the other end point of the curve has a tendency to decrease from a Nyquist diagram for the first impedance measurement at t=5 to a Nyquist diagram for the last impedance measurement at t=60.

By using the foregoing tendency, it is possible to judge that there comes a timing to carry out a recovering process on a gas sensor. Namely, a predetermined threshold for a value of reaction resistance which corresponds to R2 in FIG. 3 and is obtained by extrapolation of the curve on a real axis is determined in advance, and a value of reaction resistance is intermittently (or periodically) and repeatedly obtained at predetermined intervals by performance of impedance measurement during use of a gas sensor. When a value of reaction resistance as obtained falls below the threshold, it is judged that the timing has come. This is the method of judging necessity of a recovering process in this manner. Since only a value corresponding to R2 in FIG. 3 is to be used for diagnosis target (diagnosis parameter), it is possible to achieve diagnosis targeted only to resistance variation which occurs by a reversible cause and can be recovered by a recovering process.

Additionally, the threshold may be set at a value which is obtained from multiplication of a value of reaction resistance in the initial stage of use by a predetermined threshold coefficient α (0<α<1) until the first recovering process is carried out from a start of use of a gas sensor. After a recovering process is carried out, the threshold may be set at a value which is obtained from multiplication of the value of reaction resistance obtained by performance of impedance measurement immediately after the recovering process by the threshold coefficient α. As a result of this, after a recovering process is once carried out, necessity to carry out a recovering process again can be appropriately judged with reference to a state provided after the recovering process. A specific value of the threshold coefficient α can be determined appropriately, considering measurement accuracy which is required of a gas sensor, a composition of a sensing electrode, and the like.

(Second Manner: Judgment Based on Phase Angle)

In the above-described first manner of judgment based on a Nyquist diagram, it is required to measure impedance over a wide frequency range (a range of 0.1 Hz to 1 MHz in the case shown in FIG. 4) every time an opportunity to perform impedance measurement comes, because reaction resistance is directly obtained. Accordingly, a considerable time is required to perform impedance measurement once. Also, as generally known, a concentration of a component in an exhaust gas exhausted from an internal combustion engine is likely to vary. Thus, strictly speaking, spending a considerable time on measurement may unfavorably cause a concentration of an unburned hydrocarbon gas in a measurement target to vary by a frequency in some cases.

On the other hand, what is essentially required to judge necessity of a recovering process is to grasp a state in which reaction resistance is reduced to fall out of a predetermined tolerable range. Grasp of such a state is not necessarily achieved by directly obtaining a value of reaction resistance. Necessity of a recovering process may be judged by using a parameter correlated with reaction resistance as a diagnosis parameter, instead of reaction resistance itself.

From this point of view, in this manner, a phase angle resulted from impedance measurement is used for judgment.

Figure 5:
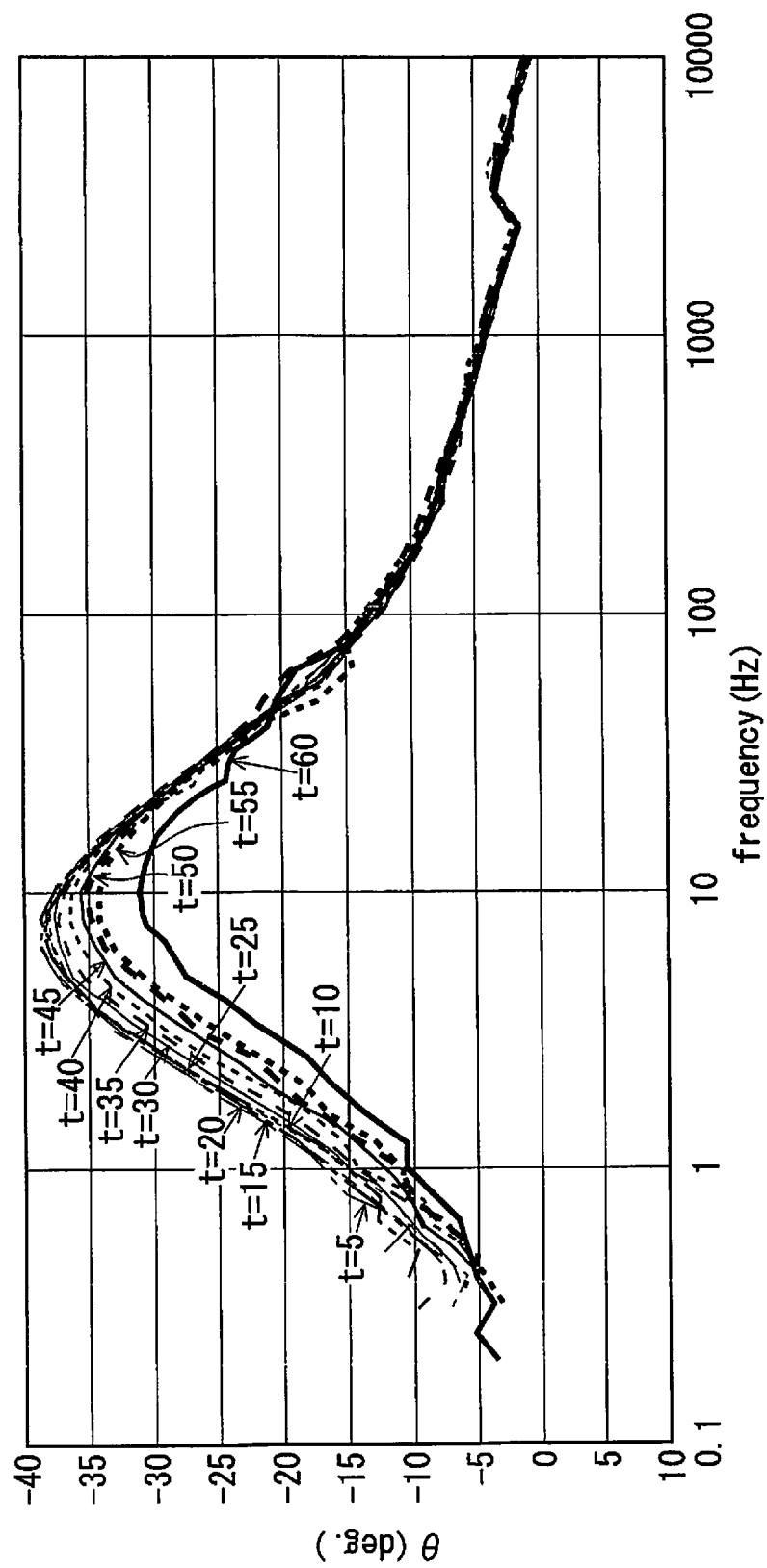
FIG. 5 is a view showing time-series variation of Bode diagrams for a phase angle θ of impedance, which are respectively obtained from results of impedance measurement performed in order to obtain the Nyquist diagrams shown in FIG. 4.

FIG. 5 is a view showing time-series variation of Bode diagrams for a phase angle θ of impedance, which are respectively obtained from results of impedance measurement performed in order to obtain the Nyquist diagrams shown in FIG. 4

From FIG. 5, it can be seen that each of the Bode diagrams has a peak value (extremum) when a frequency is in a range of approximately 7 Hz to 10 Hz, and that a peak value (extremum) has a tendency to get near to zero from a Bode diagram for the first impedance measurement at t=5, to a Bode diagram for the last impedance measurement at t=60. Such a tendency is correlated with a tendency of reaction resistance to be reduced, which is represented in the Nyquist diagrams shown in FIG. 4.

Thus, according to the present way, impedance measurement is experimentally performed in advance or in the initial stage of actual use of a gas sensor, regarding a predetermined frequency range which is wide enough to produce a Bode diagram for a phase angle θ. Then, based on a result of the impedance measurement, a Bode diagram for a phase angle θ is produced, and a frequency contributing to a peak value (extremum) is designated as a frequency used for diagnosis (which will be referred to as a "diagnosis frequency"). Also, a threshold of a phase angle θ at the diagnosis frequency is determined. Such impedance measurement is regarded as preliminary measurement in the present way.

Then, in actual use of a gas sensor, only impedance measurement in which an alternating voltage at a diagnosis frequency is applied is performed at predetermined intervals. When a value of a phase angle θ which is obtained from a result of the foregoing impedance measurement becomes closer to zero than a threshold, it can be judged that there comes a timing to carry out a recovering process on a gas sensor.

The reason for the foregoing matter is as follows. Reduction in reaction resistance and variation in peak value (extremum) in a Bode diagram for a phase angle θ are correlated with each other as described above, and so, by determining a threshold of a phase angle θ in this manner so as to be commensurate with a threshold of reaction resistance in the first manner, it is possible to judge that reaction resistance is reduced to an extent that a recovering process is necessary, without directly obtaining reaction resistance. This is a method of judging necessity of a recovering process in this manner.

Preferably, impedance measurement is performed over a wide frequency range (for example, a range of 0.1 Hz to 1 MHz) immediately after a recovering process, and a peak value (extremum) in a Bode diagram for a phase angle θ is obtained. Then, a threshold is set in accordance with the peak value (extremum). As a result of this, also in this manner, as well as the first manner, necessity to carry out a recovering process again can be appropriately judged with reference to a state provided after the recovering process.

This manner, in which only one diagnosis frequency serves as a measurement frequency used in impedance measurement performed at an appropriate point in time during actual use of a gas sensor, is advantageous over the first manner in that a time required to judge necessity of a recovering process is shortened. Because of a shorter time for measurement, for example, in a case where a gas sensor is attached to an exhaust pipe of an automobile and an exhaust gas is a measurement gas, it is preferable to carry out a diagnosing process under a condition that components of a measurement gas are settled, namely, immediately before engine starting, immediately after engine starting, at an idling time, at a fuel-cut time, or the like. This could favorably improve diagnosis accuracy.

Additionally, in FIG. 5, a frequency contributing an extremum has a tendency to increase as a value of t increases. In a case where such a tendency is empirically identified, a diagnosis frequency may be set to be slightly higher (by approximately 2 Hz in the case shown in FIG. 5) than a frequency contributing to a peak value (extremum) in a Bode diagram for a firstly-obtained phase angle θ.

(Third Manner: Judgement Based on an Absolute Value of Impedance)

According to the above-described second manner, necessity of a recovering process is judged by utilizing a peak occurring in a Bode diagram for a phase angle θ. Instead of that, necessity of a recovering process can be judged based on a Bode diagram for an absolute value $|Z|$ of impedance.

Figure 6:
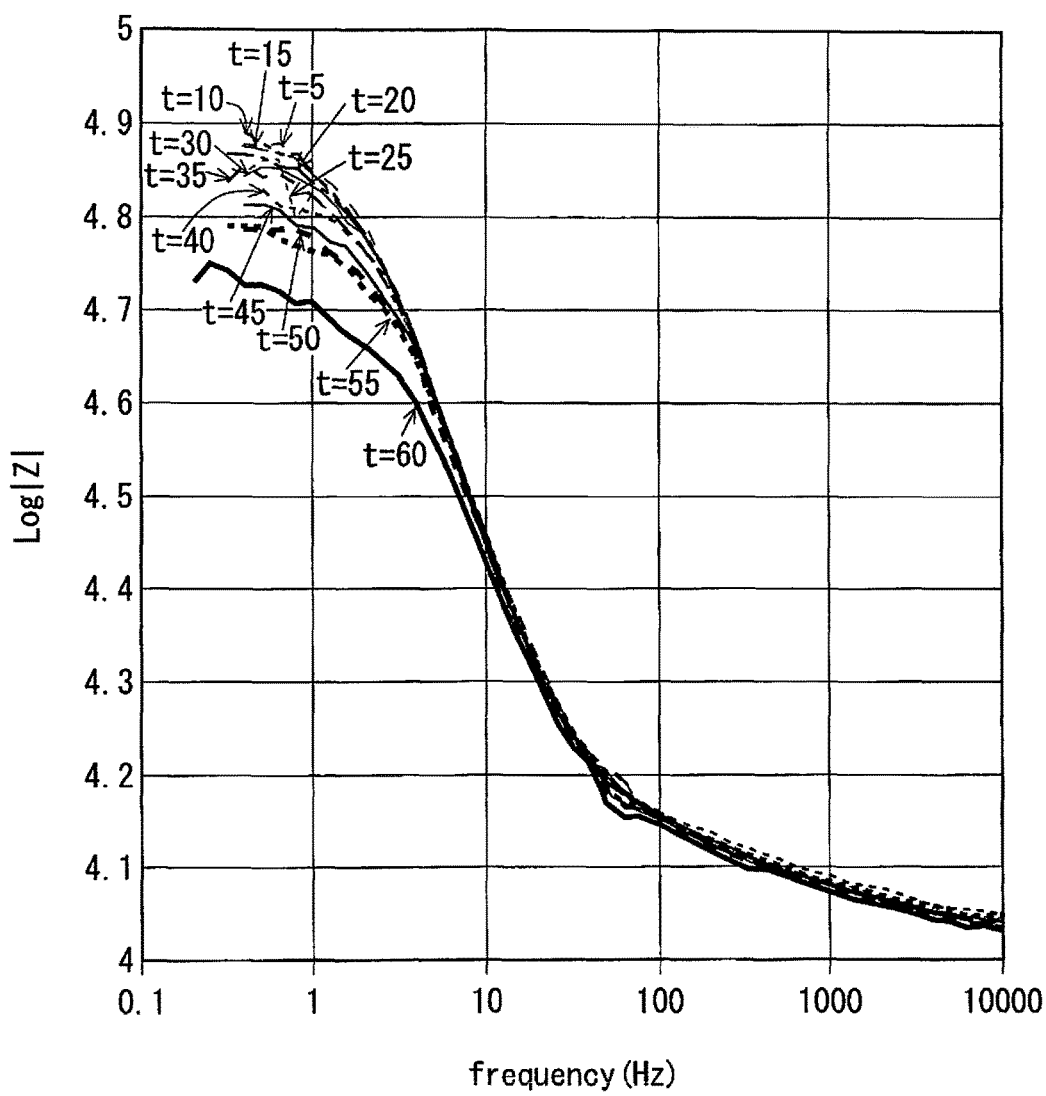
FIG. 6 is a view showing time-series variation of Bode diagrams for an absolute value |Z| of impedance, which are respectively obtained from results of impedance measurement performed in order to obtain the Nyquist diagrams shown in FIG. 4.

FIG. 6 is a view showing time-series variation of Bode diagrams for an absolute value $|Z|$ of impedance, which are respectively obtained from results of impedance measurement performed in order to obtain the Nyquist diagrams shown in FIG. 4. It is noted that a vertical axis in FIG. 6 represents a common logarithm $Log|Z|$ of an absolute value $|Z|$.

From FIG. 6, it can be seen that each of the Bode diagrams has a tendency to substantially monotonously decrease as a frequency increases. Further, all of the Bode diagrams substantially agree with one another when a frequency is in a range of approximately 10 Hz or higher.

On the other hand, when a frequency is in a range of 10 Hz or lower, a value of $Log|Z|$ has a tendency to decrease with elapse of time from a Bode diagram for the first impedance measurement at t=5 to a Bode diagram for the last impedance measurement at t=60. Such a tendency is correlated with a tendency of reaction resistance to be reduced, which is represented in the Nyquist diagrams shown in FIG. 4.

Figure 7:
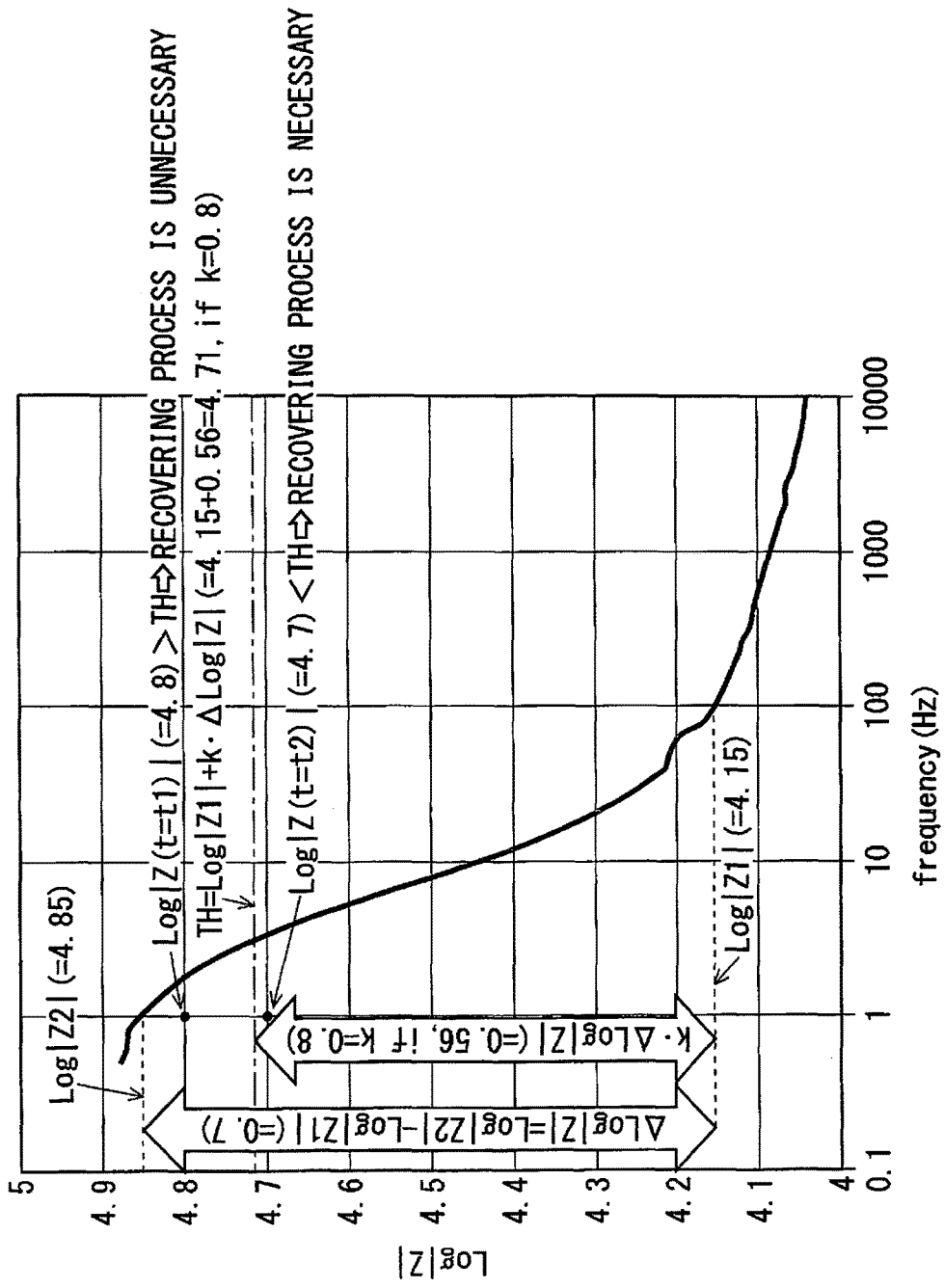
FIG. 7 is a view showing an example of a Bode diagram for an absolute value |Z| of impedance.

From this point of view, in this manner, impedance measurement is experimentally performed in advance or in the initial stage of actual use of a gas sensor, regarding a predetermined frequency range which is wide enough to produce a Bode diagram for an absolute value $|Z|$ of impedance. Then, based on a result of the impedance measurement, a Bode diagram for an absolute value $|Z|$ is produced. Such impedance measurement is regarded as preliminary measurement in the present way. FIG. 7 shows an example of the foregoing Bode diagram. Further, a value of a parameter such as a frequency used for diagnosis (which will be referred to as a "diagnosis frequency") is previously specified based on the foregoing Bode diagram.

More specifically, when the Bode diagram as shown in FIG. 7 is obtained by impedance measurement, a frequency at which an absolute value $|Z|$ is considered to be substantially unchanging in the Bode diagram despite elapse of time (which will be hereinafter referred to as a "reference frequency") is specified. Also, one of frequencies in the vicinity of a frequency which contributes to a maximum of $Log|Z|$ is designated as a diagnosis frequency. Further, a value $Log|Z1|$ of $Log|Z|$ at a reference frequency and a value $Log|Z2|$ of $Log|Z|$ at a diagnosis frequency are specified.

In the case shown in FIG. 7, a reference frequency is set at 100 Hz, and a diagnosis frequency is set at 1 Hz. As a result of this, $Log|Z1|$ is equal to 4.15, and $Log|Z2|$ is equal to 4.85.

Further, a threshold coefficient k by which a value of difference between $Log|Z1|$ and $Log|Z2|$, i.e., Δ

$Log|Z|=Log|Z2|-Log|Z1|$, is multiplied, is determined. In this regard, a threshold coefficient k is a value satisfying $0<k<1$, and a value which indicates to what extent decrease of $Log|Z|$ which is caused as a gas sensor continues to be used as shown in FIG. 6 can be allowed with respect to a value of difference Δ $Log|Z|$. By determining the threshold coefficient k such that an allowable decrement of $Log|Z|$ is commensurate with a threshold of reaction resistance in the first manner, it is possible to judge that reaction resistance is reduced to an extent that a recovering process is necessary, without directly obtaining reaction resistance.

Actually, during actual use of a gas sensor, only impedance measurement in which an alternating voltage at a diagnosis frequency is applied is performed. Then, when a value of $Log|Z|$ at the diagnosis frequency becomes equal to, or smaller than, a threshold determined by an expression of $TH=Log|Z1|+k\cdot\Delta\ Log|Z|$, it is judged that a recovering process is necessary.

The case shown in FIG. 7 is an example where the threshold coefficient k is set at 0.8 (80%). Also, Δ $Log|Z|=Log|Z2|-Log|Z1|$ is equal to 0.7. Accordingly, when a value of $Log|Z|$ at a frequency of 1 Hz which is a diagnosis frequency falls below $TH=4.15+0.8\times0.7=4.71$, it is judged that a recovering process is necessary.

For example, when values of $Log|Z|$ at t=t1, t2 (t1<t2) are represented as $Log|Z\ (t=t1)|$ and $Log|Z\ (t=t2)|$, respectively, the following expressions are formulated in the case shown in FIG. 7: $Log|Z\ (t=t1)|=4.8>TH$; and $Log|Z\ (t=t2)|=4.7<TH$. Thus, it is judged that while a recovering process is unnecessary at t=t1, a recovering process is necessary at t=t2.

Preferably, impedance measurement is performed over a wide frequency range (for example, a range of 0.1 Hz to 1 MHz) immediately after a recovering process, and a Bode diagram for an absolute value $|Z|$ of impedance is obtained. Then, a value of a threshold TH is determined based on the Bode diagram as obtained. As a result of this, also in this manner, like the first manner, necessity to carry out a recovering process again can be appropriately judged with reference to a state provided after the recovering process.

This manner, like the second manner, in which only one diagnosis frequency serves as a measurement frequency used in impedance measurement performed at an appropriate point in time during actual use of a gas sensor, is advantageous over the first manner in that a time required to judge necessity of a recovering process is shortened. Because of a shorter time for measurement, in this manner, also like the second manner, it is preferable to carry out a diagnosing process under a condition that components of a measurement gas are settled. This could favorably improve diagnosis accuracy.

As described above, according to the present preferred embodiment, necessity of a recovering process for recovering an output which varies due to reversible deterioration occurring in a sensing electrode of a mixed-potential gas sensor can be judged based on an extent of the reversible deterioration occurring in the sensing electrode. Therefore, it is possible to carry out a recovering process at a suitable timing.

MODIFICATIONS

While in the above-described preferred embodiment, only the gas sensor 100A is described as an example of a gas sensor to be diagnosed, a gas sensor having another configuration can be a target to be diagnosed.

Though a diagnosing process is carried out based on a result of impedance measurement in which an alternating voltage is applied between a sensing electrode and a reference electrode in the above-described preferred embodiment, a diagnosing process may be carried out alternatively based on resistance variation which is caused when a direct voltage is applied (variation in resistance by direct-current measurement). For example, a current flowing when 0 V is applied between a sensing electrode and a reference electrode and a current flowing when 0.1 V is applied between those electrodes are measured, and resistance (direct-current resistance) is obtained from a slope of a voltage-current line (VI line) which is specified based on results of measurement of the two currents. Then, a diagnosing process may be carried out in such a manner that it is judged that a recovering process is necessary when the resistance as obtained becomes equal to, or smaller than, a predetermined threshold, or the like manner.

While the above-described preferred embodiment deals with a case where an exhaust gas present within an exhaust pipe of an internal combustion engine such as a diesel engine or a gasoline engine is a measurement gas and a concentration of an unburned hydrocarbon gas in the measurement gas is determined, a target to be measured by the gas sensor 100A is not limited to a hydrocarbon gas. The gas sensor 100A can measure also $NH_3$ and $NO_x$ based on principles of mixed potential in a similar way to the above-described ways in the above-described preferred embodiment.

Also, while each of a sensing electrode and a reference electrode is provided as a cermet electrode formed of a noble metal (more specifically, Pt—Au alloy for a sensing electrode and Pt for a reference electrode) and zirconia in the above-described preferred embodiment, a sensing electrode may alternatively be formed of an oxide of at least one kind of metals including Cu, Zn, Sn, La, Nb, Sr, Ti, Si, Cr, In, Cd, Ni, W, V, Fe, Tb, Bi, Ta, Y, Ga, Mo, and Co, or a complex oxide which is a mixture of some of oxides of those metals. Those oxides and complex oxides do not serve as a combustion reaction catalyst of a measurement gas, so that electrochemical reaction is caused in a three-phase interface.

Example

With the use of two different gas sensors 100A (which will be hereinafter referred to as a "sensor No. 1", and a "sensor No. 2"), effects of a recovering process based on a diagnosing process were confirmed.

More specifically, each of the two gas sensors 100A was continuously driven while the sensing electrode 10 was kept exposed to a gas atmosphere containing an unburned hydrocarbon gas and a temperature of a sensor element was set at 600° C., and a diagnosing process was carried out according to the third manner. Then, a procedure of carrying out a recovering process immediately after it was judged that a recovering process was necessary was repeated.

A gas atmosphere is as follows (produced with the use of a model gas apparatus):
$C_2H_4$ (corresponding to an unburned hydrocarbon gas)=2000 ppm (4000 ppmC);
$O_2$=10%;
$H_2O$=5%; and
$N_2$=residual.

A diagnosis frequency was set at 1 Hz, and impedance measurement for a diagnosing process was performed with the use of a known impedance analyzer at 100-second intervals (at 100-second intervals after a recovering process in a case where a recovering process was carried out). Also, impedance measurement had previously been performed in a range of 0.1 Hz to 1 MHz, so that the initial threshold TH was set at 4.82 for the sensor No. 1, and the initial threshold TH was set at 4.80 for the sensor No. 2.

Additionally, a concentration of $C_2H_4$ in the gas atmosphere was set at 4000 ppmC which was higher than a concentration of an unburned hydrocarbon gas in an exhaust gas exhausted from a general internal combustion engine, in order to accelerate adsorption of $C_2H_4$ into the sensing electrode 10. Also, a measurement interval for impedance measurement was set at every 100 seconds in accordance with such acceleration of adsorption, and a longer measurement interval may be set for actual use of a gas sensor.

A recovering process was carried out with the sensor element 101A being heated for 30 seconds at a heating temperature of 850° C. by the heater part 70.

Figure 8:
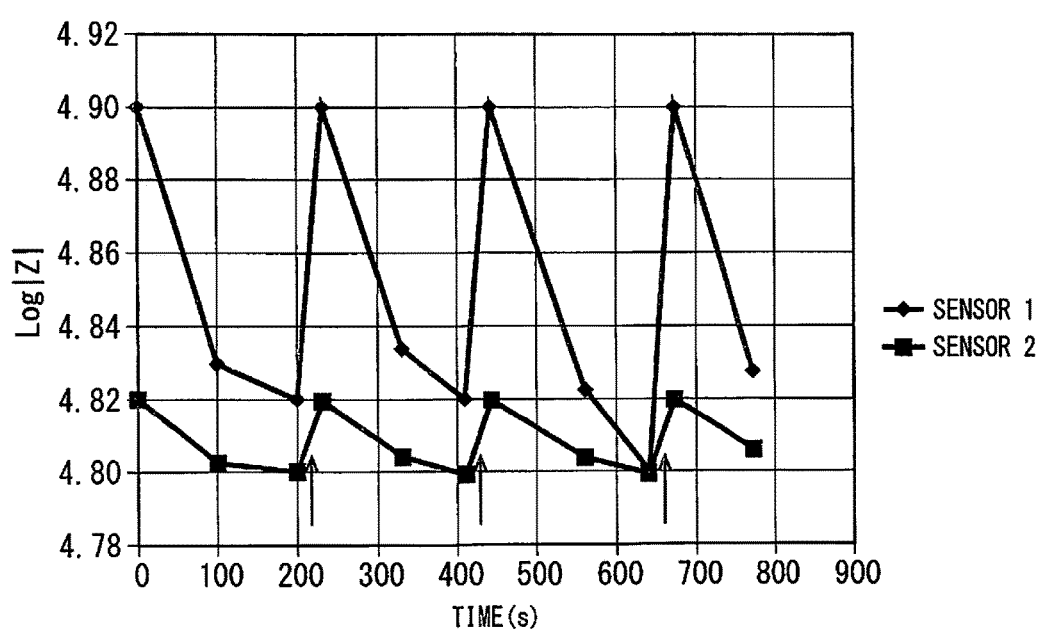
FIG. 8 is a view showing variation of Log|Z| with time, for a sensor 1 and a sensor 2.

FIG. 8 is a view showing time-series variation of a logarithm Log|Z| of an absolute value |Z| of impedance for each of the sensors No. 1 and the sensor No. 2 after a start of driving the sensors. It is noted that the sensor No. 1 and the sensor No. 2 are depicted simply as "SENSOR 1" and "SENSOR 2", respectively, in FIG. 8. The initial values of Log|Z| of the gas sensors 100A are 4.90 and 4.82, respectively.

In each of the sensor No. 1 and the sensor No. 2, a value of Log|Z| became equal to, or smaller than, a value TH thereof when 200 seconds had passed, and immediately after that, a recovering process was carried out at a point in time indicated by an arrow in FIG. 8. Immediately after the recovering process, impedance measurement was performed, which indicated that Log|Z| was identical to the initial value. Accordingly, the respective values of thresholds TH for the sensor No. 1 and the sensor No. 2 were set at values identical to the respective initial values.

Thereafter, in the same manner as described above, a diagnosing process at 100-second intervals and a procedure of carrying out a recovering process at a point in time indicated by an arrow in FIG. 8 when the value of Log|Z| became equal to, or smaller than, a value of TH, were repeated. In a range of up to 900 seconds shown in FIG. 8, a value of Log|Z| provided after a recovering process agreed with an initial value.

While the invention has been shown and described in detail, the foregoing description is in all aspects illustrative and not restrictive. It is therefore understood that numerous modifications and variations can be devised without departing from the scope of the invention.

What is claimed is:

1. A gas-sensor diagnosing method of judging necessity of a recovering process carried out on a mixed-potential gas sensor for recovering an output of said gas sensor, said method comprising the steps of:
    (a) performing impedance measurement between a sensing electrode exposed to an atmosphere of a measurement gas and a reference electrode exposed to a reference atmosphere, said sensing electrode and said reference electrode being provided in said gas sensor; and
    (b) judging necessity of said recovering process based on electrode reaction resistance in said gas sensor or a diagnosis parameter which is a parameter correlated with said electrode reaction resistance, said electrode reaction resistance and said diagnosis parameter being obtained based on a result of said impedance measurement, wherein
    said step (a) and said step (b) are intermittently or periodically repeated during use of said gas sensor, and it is judged that said recovering process is necessary when said diagnosis parameter satisfies a predetermined threshold condition in said step (b), and
    in said step (b), when said recovering process is carried out after it is judged that said recovering process is necessary, said threshold condition is re-set based on a value of said diagnosis parameter which is provided immediately after said recovering process.

2. The gas-sensor diagnosing method according to claim 1, wherein
    in said step (a), said impedance measurement is performed by application of an alternating voltage between said sensing electrode and said reference electrode with a frequency being varied within a frequency range in which a Nyquist diagram for said electrode reaction resistance is allowed to be produced, and
    in said step (b), said electrode reaction resistance is calculated based on said Nyquist diagram produced based on a result of said impedance measurement, and it is judged that said recovering process is necessary when said electrode reaction resistance is equal to, or smaller than, a predetermined threshold.

\* \* \* \* \*